United States Patent
Zheng

(10) Patent No.: US 8,263,057 B2
(45) Date of Patent: Sep. 11, 2012

(54) MASCARA COMPOSITION CONTAINING SHAPE-MEMORY POLYMERS, GELS, AND FIBERS

(75) Inventor: Tao Zheng, Nanuet, NY (US)

(73) Assignee: Avon Products, Inc., New York, NY (US)

( * ) Notice: Subject to any disclaimer, the term of this patent is extended or adjusted under 35 U.S.C. 154(b) by 1280 days.

(21) Appl. No.: 11/959,321

(22) Filed: Dec. 18, 2007

(65) Prior Publication Data

US 2008/0145428 A1 Jun. 19, 2008

Related U.S. Application Data

(60) Provisional application No. 60/875,463, filed on Dec. 18, 2006.

(51) Int. Cl.
*A61Q 19/00* (2006.01)
*A61Q 1/10* (2006.01)

(52) U.S. Cl. ............... 424/78.02; 424/70.7; 424/401

(58) Field of Classification Search .................. None
See application file for complete search history.

(56) References Cited

U.S. PATENT DOCUMENTS

| 5,155,199 A | 10/1992 | Hayashi |
| 2005/0013838 A1* | 1/2005 | De La Poterie ............... 424/401 |
| 2006/0134038 A1 | 6/2006 | De la Poterie et al. |

FOREIGN PATENT DOCUMENTS

| EP | 1038519 A1 | 9/2000 |
| EP | 1682602 A1 | 7/2007 |
| JP | 07126125 A1 | 5/1995 |
| WO | 03084489 A1 | 10/2003 |

* cited by examiner

*Primary Examiner* — Jyothsna Venkat
(74) *Attorney, Agent, or Firm* — Joan M. McGillycuddy; David M. Joyal; Charles J. Zeller

(57) ABSTRACT

Cosmetic compositions containing an eyelash curling or branching agent, or a skin-lifting mask or lotion. The mascara composition comprises a SMP, at least one film-forming polymer and at least one wax and leads to a make-up product with good staying power, as well as good coating and curling. The skin-lifting mask or lotion comprises a SMP, a water phase and an oil phase and leads to a make-up product with a skin-lifting effect. The invention also pertains to a process for coating eyelashes which consists of applying the composition to the eyelashes with heat.

2 Claims, 2 Drawing Sheets

Eyelash before SMP mascara application, at ambient temperature.

Eyelash after SMP mascara application, at ambient temperature.

Eyelash with SMP mascara heated by applicator, at 50 °C.

8,263,057 B2

MASCARA COMPOSITION CONTAINING SHAPE-MEMORY POLYMERS, GELS, AND FIBERS

This application claims priority to U.S. Provisional Patent Application Ser. No. 60/875,463, filed Dec. 18, 2006, the entire contents of which are hereby incorporated by reference herein.

FIELD OF THE INVENTION

The present invention relates to a cosmetic composition, such as a mascara, having at least one shape-memory polymer, gel, or fiber included therein.

BACKGROUND OF THE INVENTION

Shape memory substances are able to be deformed into a temporary configuration and then restored to the original parent geometry by application of stimuli such as temperature, light, force, chemicals and electrical. The thermally induced shape-memory effect has been described for different material classes: polymers, such as polyurethranes, poly (styrene-block-butadiene) and polynorbornene, hydrogels, metallic alloys, and ceramics. Shape-memory alloys such as nickel-titanium have been widely used since the 1930s in robots, satellites, medical devices, actuators and other areas.

First introduced in Japan and then the United States in 1984, shape-memory polymers (SMP) have been used in the biomedical area for medical stents and sutures. Unlike shape-memory alloys, SMP have improved properties such as easy shaping, high shape stability, and adjustable transition temperature. Above their transition temperature (Ttrans), SMP cars be stretched, folded, or otherwise conformed to other shapes, tolerating up to 200% elongation. The process can be repeated many tunes without losing material integrity. The "memory" or recovery comes from the stored mechanical energy attained during the reconfiguration and cooling of the material. Some SMP recover shape not by heat but by changes in pH, electrical stimuli, or light stimuli. Some SMP are based on styrene acrylate, cyanate ester, and epoxy polymer systems.

SMP have been used in hair styling products for hair setting and skin and face makeup products for bioactive delivery. WO Publication No. 2003084489 and EP Patent No. 1682602 to Mnemoscience GmbH describe a hair care composition comprising SMP, alone or combined with cationic active ingredients to shape hair. JP 07126125 and U.S. Pat. No. 5,155,199 to Mitsubishi Heavy Industries Ltd. describe a cosmetic makeup composition containing shape-memory resin (polyurethane) spherical particles having a glass transition temperature lower than the skin surface temperature. However, SMP have not been used in other cosmetic products, such as mascaras, face-lifting skin masks or wrinkle reducing creams.

For example, mascara products have been marketed that curl or branch eyelashes. Unfortunately, eyelash curling and branching are difficult to achieve, requiring polymer film formers and fibers, and the effects are of short duration and lost under external influences such as eye blinking, high humidity, or contact with tears. Moreover, scissor type devices for curling eyelashes require a crimping process which both requires dexterity to result in a satisfactory crimp and which may result in pinching of fee eyelid, pulling and overcurling. Heating the eyelash curling device via a remote heating device such as a blow dryer has been used to curl the eyelashes more easily and permanently with these devices. Plunger type devices for curling eyelashes cannot be used by one hand and are designed for a person to perform the curling treatment on someone else.

Novel, safe and effective topical mascara compositions for curling or branching eyelashes are needed. The need exists for alternative methods to provide eyelash curling and branching which overcomes the problems associated with previous methods and compositions and which would represent a significant advance in cosmetic art.

The present invention provides for the use of SMP in mascaras, skin-lifting mask or lotion cosmetic compositions. None of the existing art provides the advantages and benefits of the present invention.

It is an object of the present invention to provide long-lasting ending or branching mascara compositions containing SMP.

It is another object of the present invention to provide face mask or face lifting compositions containing SMP.

It is yet another object of the present invention to provide a mascara composition containing a SMP, at least one wax and at least one film-forming polymer.

It is yet another object of the present invention to provide a skin lifting mask or lotion composition containing a SMP, an oil phase and a water phase.

It is a further object of the present invention to provide a method for curling eyelashes comprising applying the composition containing a SMP to the eyelashes.

It is a further object of the present invention to provide a method for producing a skin-lifting effect comprising applying the composition containing a SMP to the skin.

SUMMARY OF THE INVENTION

In accordance with the foregoing objectives and others, the present invention provided methods for curling eyelashes which includes applying a curling composition with heat to the eyelashes, and for skin lifting which includes applying a skin lifting mask or lotion composition with heat.

In one aspect, a method is provided for imparting a curling or branching effect to eyelashes comprising: (i) applying to said eyelashes a composition comprising a thermally activated shape memory polymer (SMP) having a transition temperature ($T_{trans}$); (ii) increasing the temperature of said SMP to a temperature at or above $T_{trans}$; and (iii) cooling said SMP to a temperature below $T_{trans}$. In the preferred practice, the transition temperature ($T_{trans}$) is above 20° C. The SMP has a modulus of elasticity which is lower at temperatures above $T_{trans}$ than at temperatures below $T_{trans}$, and typically the ratio of the modulus of elasticity below $T_{trans}$ to above $T_{trans}$ is at least 1.1.

There is essentially no constraint on the nature of the SMP. It may be, for example, a thermoplastic polyurethane elastomer and in particular a block copolymer of PEO-PFO-PEO with urethane/urea units in certain embodiments. The SMP may be a one-way thermally induced SMP or a two-way thermally induced SMP.

The temperature increase is may be achieved by any suitable method, including, for example, by applying an external source of heat to the SMP with a hot air or a heated mascara curler, or the like. The SMP will typically be formulated as a mascara product and therefore may be applied to the lashes in conjunction with other ingredients such as, for example, at least one film-forming polymer and at least one wax. The inventive composition which is applied to the lashes may comprises; (i) about 0.1% to about 50% by weight of SMP; (ii) about 0.1% to about 50% by weight of at least one film-forming polymer; (iii) about 0.1 to about 50% by weight of at least one wax; and (iv) a cosmetically acceptable vehicle, the vehicle typically being water-based.

Also provided is a method for lifting the skin of the face comprising: (i) applying to the skin of the face of an individual in need thereof, a gel composition comprising a thermally activated shape memory polymer (SMP), the gel being swollen at temperatures below the lower critical solution temperature (LCST); and (ii) increasing the temperature of said gel above the LCST to thereby shrink said gel composition, resulting in a skin-lifting effect. The inventive gel composition may be a hydrogen comprising; (i) about 1% to about 60% by weight of the SMP, typically from about 5% to about 20%; (ii) about 1% to about 50% by weight of an oil phase; and (iii) about 10 to about 99% by weight of a water phase. One SMP which has been found useful according to this aspect of the invention is a co-polymerized acrylic acid and stearyl acrylate cross-linked with methylenebisacryl amide and sodium acrylate, in which case the LCST is about 37° C.

These novel features of the present invention will become apparent to those skilled in the art from the following detailed description, which is simply, by way of illustration, various modes contemplated for carrying out the invention. As will be realised, the invention is capable of additional, different obvious aspects, all without departing from the invention. Accordingly, the specification is illustrative in nature and not restrictive.

DETAILED DESCRIPTION OF THE INVENTION

Figure 1:
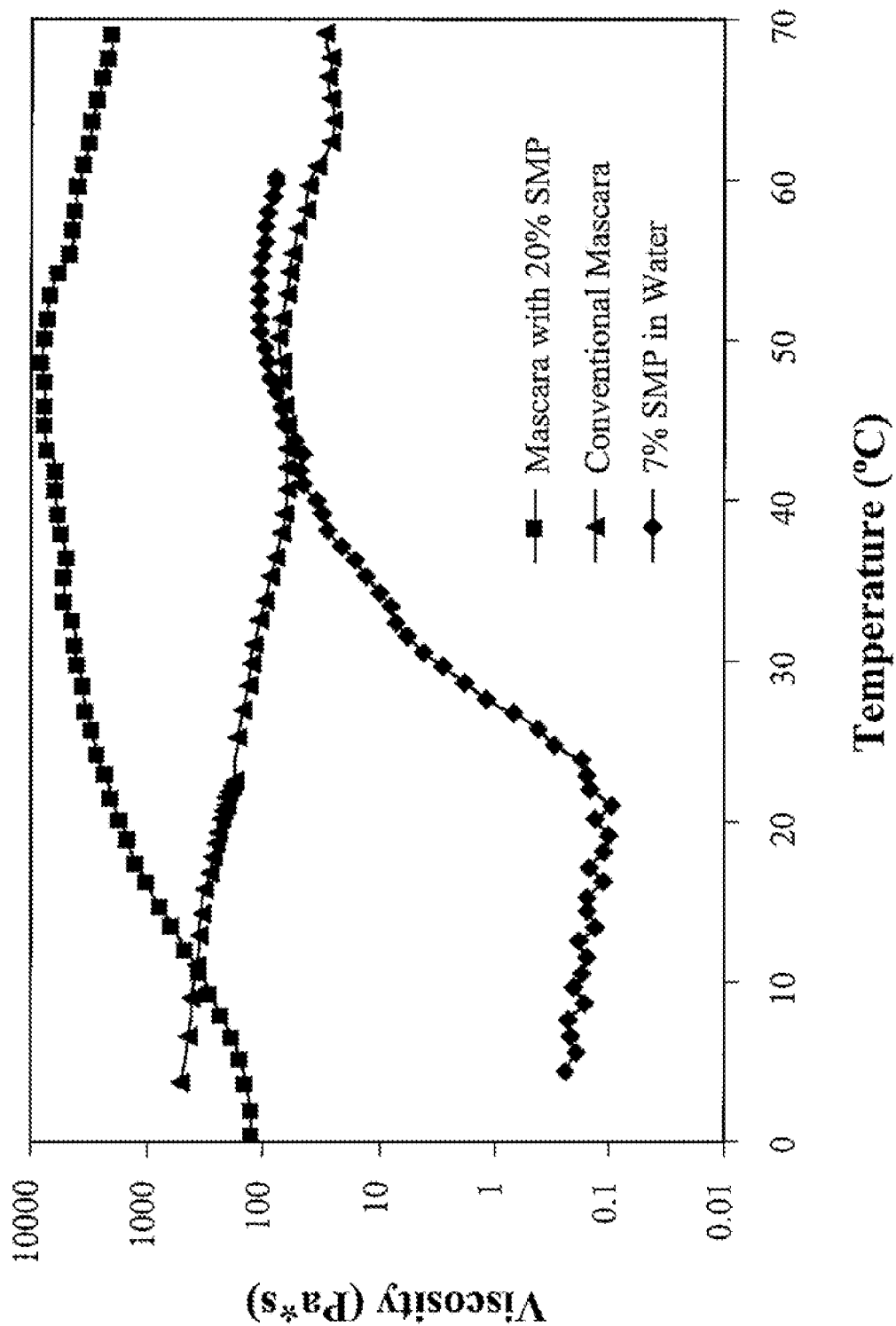
FIG. 1 shows rheology profiles of mascara compositions with and without SMP, as well as SMP solution in water.

By "shape memory" material is meant a material that can recover its primary shape after being deformed when it is heated or receives any other external stimuli, such as temperature, light, pH, and mechanical forces.

The phrase "cosmetically acceptable vehicle" refers to a medium that is compatible with keratin materials, such as human skin.

For the purposes of the invention, the terns "polymer" means a compound containing at least two repeating units, such as, for example, a compound containing at least three repeating units, which may be identical.

The term "dispersal" as used herein refers to any process by which tire ingredients are uniformly distributed in the emulsified base, and includes dissolving, emulsifying, and forming a colloidal suspension or gel.

As used herein the term "effective amount" refers to an amount sufficient to result in curling of the eyelashes and lifting of the appearance of the skin.

The terms "a" and "an", as used herein and in the appended claims, mean "one or more" unless otherwise indicated herein.

It should be noted that unless indicated to the contrary, as used herein, percent (%) is % by weight, based on the total weight of the composition.

The term "film-forming polymer" as referred to herein means a polymer which by itself, or in the presence of a plasticizer, upon drying produce a continuous film on skin, hair or nails (CTFA International Cosmetic Ingredient and Dictionary, 8th ed., 1999).

One preferred embodiment of the composition is a mascara composition. Embodiments of the present invention provide a mascara composition containing SMP which provide a long-lasting curling or branching effect induced by temperature change. In particular embodiment, the curling or branching effect is induced by an increase in temperature of the mascara composition containing SMP.

The mascara composition may take the form of an emulsion or gel or dispersion of SMP, film-forming components and waxes in water or other carriers. Alternatively, the composition may be in the form of a solid, such as a mascara cake or soap.

The shape memory effect results from the polymer's structure and morphology. The effect is persistent in many polymers, which might differ significantly in their chemical composition.

Any suitable thermoresponsive SMPs or their derivatives thereof that achieve the desired effect may be employed. Depending upon the type of cosmetic composition, e.g. mascara or skin lifting mask or lotion, a single SMP or mixture of SMPs will be used.

Preferably, the SMP include physical crosslinked, chemical crosslinked, and biodegradable SMP systems. Examples of polymers used to prepare hard and soft segments of SMPs include various polyethers, polyacrylates, polyamides, polysiloxanes, polyurethanes, polyether amides, polyurethane/ureas, polyether esters, and urethane/butadiene copolymers.

Suitable shape memory polymers include but are not limited to those described in WO 03/084489; U.S. Pat. No. 5,506,300 to Ward et al.; U.S. Pat. No. 5,145,935 to Hayashi; U.S. Pat. No. 5,665,822 to Bitler et al.; and Gorden, "Applications of Shape Memory Polyurethanes," Proceedings of the First International Conference on Shape Memory and Superelastic Technologies, SMST International Committee, pp. 115-19 (1994); U.S. Pat. No. 6,160,084 to Langer; U.S. Pat. No. 6,388,043 to Langer, Kim, et al., "Polyurethanes having shape memory effect," Polymer 37(26):5781-93 (1996); Li et al., "Crystallinity and morphology of segmented polyurethanes with different soft-segment length," J Applied Polymer 62:631-38 (1996); Takahashi et al, "Structure and properties of shape-memory polyurethane block copolymers," J. Applied Polymer Science 60:1061-69 (1996); Tobushi H., et al., "Thermomechanical properties of shape memory polymers of polyurethane series and their applications," J Physique IV (Colloque C1) 6:377-84 (1996)), the contents of which are incorporated by reference herein in their entirety.

Other SMPs are described in U.S. Pat. No. 5,155,199, JP 07126125, WO 2003/084489, and EP 1682602, the disclosure of which are hereby incorporated by reference herein.

Examples of suitable physical crosslinked SMP include, but are not limited to, linear block copolymers, such as thermoplastic polyurethane elastomers with hard segment as permanent shape and soft segment as switching temporary shape. Multiblock copolymers can also serve as SMP, such as polyurethanes with a polystyrene and poly(1,4-butadiene), ABA triblock copolymers of poly(tetrahydrofuran) and poly(2-methyl-2-oxazoline), polynorbornene, polyhedral oligomeric silsequixane (POSS)-modified polynorbornene, and PE/Nylon-6 grafted copolymer.

Examples of suitable chemical crosslinked shape-memory polymers include, but are not limited to, HDPE, LDPE, copolymer of PE and polyvinyl acetate.

Examples of suitable biodegradable SMP are polyhydroxycarboxylic acids and linear multiblock copolymer of poly(p-dioxanone) and poly[ε-lactide)-co-glycolide].

Commercially available thermoplastic SMP include, but are not limited to, polyacrylates such as the PMMA and JTbu series (Polymer-Expert), cycloaliphatic polyutherurethane Tecoflex EG72D® (TFX) (Noveon), polyurethane foam of polyether polyol series—Diary, including the MM type, MP type, MS type and MB (microbead powder) type series (Mitsubishi Heavy Industries, also known as Diaplex Co. Ltd. in the U.S). Preferred is the MB series, and more preferred is MB5520 in powder form from Diaplex Co. Ltd. Commercially available shape-memory fiber products include, but are not limited to, Calo-Mer® (Polymertech).

The mascara composition of the present invention comprises water, and emulsified and dispersed in the water: an SMP; at least one film-forming polymer component; and at least one wax component.

A preferred mascara composition according to the present invention comprises: water, and emulsified and dispersed in the water:
(1) about 0.1% to about 50% of a SMP;
(2) about 0.1% to about 50% of at least one film-forming polymer; and
(3) about 0.1 to about 50% of at least one wax.

The compositions may comprise about 0.01% to about 70%, 0.05% to about 60%, about 0.1% to about 50%, about 0.5% to about 40%, about 1% to about 30%, about 2% to about 30%, about 1% to about 20%, about 2% to about 20%, about 2% to about 15%, about 2% to about 10%, about 2% to about 5%, about 5% to about 20%, about 10% to about 20%, about 15% to about 20%, about 10% to about 40%, about 15% to about 35%, or about 20% to about 30%, relative to the total weight of the composition, of one or more SMPs.

While it is understood that the SMP may be used alone, in addition to the SMP, tire mascara composition may also contain additional materials such as at least one film-forming agent. The film-forming polymer improves the wear of the composition, and can confer transfer-resistance to the make-up product. The film-forming agent may be any which is cosmetically acceptable for use around the eye. Examples include polymers such as polyethylene polymers, PVP, copolymers of PVP, ethylene vinyl acetate, dimethicone gum, C1-C6 alkyl (meth)acrylate polymer, polyacrylates, polymethacrylates, cellulose polymers, and resins such as trimethylsiloxysilicate. The film former is used in an amount of from about 0.1% to about 50%, more preferably from about 1 to about 30%. The compositions may comprise about 0.1% to about 50%, about 0.5% to about 40%, about 1% to about 30%, about 2% to about 30%, about 1% to about 20%, about 2% to about 20%, about 2% to about 15%, about 2% to about 10%, about 2% to about 5%, about 5% to about 20%, about 10% to about 20%, about 15% to about 20%, about 10% to about 40%, about 15% to about 35%, or about 20% to about 30%, relative to the total weight of the composition, of one or more film-forming polymers. Particularly preferred film-formers are PVP and sodium polyacrylate.

The mascara compositions may also contain at least one wax. The wax makes it possible to soften the composition deposited on the eyelashes. The wax may be natural or synthetic. Examples of suitable waxes include, but are not limited to, paraffin waxes, carnauba wax, beewax, rice bran wax, ouricury wax, candililla wax, montan waxes, sugarcane waxes, and polyethylene waxes. Preferred waxes include beewax, carnauba wax and paraffin wax. The wax is present in an amount of from about 0.1% to about 50%, more preferably from about 1% to about 20%, relative to the total weight of the composition. The compositions may comprise about 0.1% to about 50%, about 0.5% to about 40%, about 1% to about 30%, about 2% to about 30%, about 2% to about 25%, about 1% to about 20%, about 2% to about 20%, about 2% to about 15%, about 2% to about 10%, about 2% to about 5%, about 5% to about 20%, about 10% to about 20%, about 15% to about 20%, relative to the total weight of the composition, of one or more waxes. The composition according to the invention can also contain a mixture of waxes as defined above.

The composition may also contain an emulsifier component which can comprise at least one emulsifier selected from the group consisting of triethanolamine and a glyceryl ester. The glyceryl ester is selected from the group consisting of glyceryl stearate, glyceryl palmitate, glyceryl arachidate, lanolin waxes, macrocrystalline waxes, ozokerites, spermacetis, polyethylene waxes, hydrogenated plant oils such as jojoba waxes, and mixtures thereof A preferred glyceryl ester is glyceryl stearate. Preferably, the emulsifier component contains triethanolamine and glyceryl stearate. The compositions may comprise about 0.01% to about 25%, about 0.01% to about 20%, about 0.05% to about 15%, about 0.1% to about 15%, about 0.5% to about 15%, about 1% to about 12%, about 1% to about 10%, relative to the weight of the total composition, of an emulsifier component. The emulsifier component may comprise about 0.01% to about 25%, about 0.01% to about 20%, about 0.05% to about 15%, about 0.1% to about 15%, about 0.1% to about 10%, about 0.1% to about 5%, about 0.1% to about 4%, about 0.1% to about 3%, about 0.1% to about 2%, relative to the weight of the total composition, of triethanolamine. The emulsifier component may comprise about 0.01% to about 25%, about 0.01% to about 20%, about 0.05% to about 15%, about 0.5% to about 15%, about 0.5% to about 10%, about 1% to about 10%, about 1% to about 6%, about 1% to about 4%, relative to the weight of the total composition, of glyceryl stearate. Most preferably, the triethanolamine comprises from about 0.1% to about 4% of the composition and the glyceryl stearate comprises from about 1% to about 6%.

Viscosifying agents such as gellants may also be used. Examples include, bentone, triglycerides, aluminum stearate, C18-C36 acid glycol esters, glyceryl tribehenatc, glycerol monostcarate, alginates, carbomers, celluloses, gums, carageenans, starches or silicates. Fillers can also optionally be added, in an amount from about 1% to about 20%, preferably from about 1% to about 10%. Examples of fillers include silica, PMMA, nylon, alumina, barium sulfate, or any other filler typically used in such compositions.

The compositions may comprise about 1% to about 90%, about 2% to about 80%, about 5% to about 85%, about 10% to about 80%, about 20% to about 70%, about 30% to about 60%, about 40% to about 60%, relative to the weight of the total composition, of water. Generally, the amount of water present in the composition of the invention is at least about 40%, preferably about 50%.

The ingredients are dispersed in an emulsified composition by the method of preparation discussed below.

All ingredients useful herein may be categorized or described by their postulated mode of action. However, it is to be understood that the ingredients can, in some instances, provide more than one cosmetic and/or therapeutic benefit or operate via more than one mode of action. Therefore, classifications herein are made for the sake of convenience and are not intended to limit an ingredient to the particularly stated application or applications listed.

Thermoresponsive SMPs consist of two polymer components and resulting two phases, one with a higher transition temperature ($T_{trans}$) than the other. SMPs assume a permanent shape which can be deformed to produce other shapes. First, the SMP is produced to receive its permanent shape. In addition or in lieu of heating, deforming the SMP to its temporary shape, i.e. programming, may include cold drawing and/or deforming.

A permanent shape can be "stored" in the system while it takes the induced temporary shape. Having one permanent shape and many temporary shapes is defined as a one-way shape memory effect. Most SMPs have at least two separate phases, particularly polyurethanes. The phase responsible for the highest thermal transition, such as the highest melting point among all the phases, is the basis for the permanent shape.

Most of the thermoresponsive SMPs have a one-way shape memory effect: they remember one permanent shape formed at the higher temperature, while many temporary shapes are possible at lower temperatures for which the systems do not have any memory. A two-way thermally induced SMP will remember two permanent shapes, one formed at higher temperature and one formed at lower temperature. By thermally cycling the system, these types of polymeric materials will take two different shapes depending on the temperature. Bi-component fibers with substantially different coefficients of thermal expansion (CTE) can also produce thermally-induced shape memory effects via one structurally engineering the fiber rather than engineering the polymer. Bi-component fibers also have two distinct phases or layers, one with a high CTE and one with a low CTE phase.

Macromers or pre-polymers in accordance with the present invention which can be crosslinked in order to provide shape-memory polymers, are polymers or oligomers wherein the fixation of an impressed, permanent shape occurs by means of chemical bonds connecting specific polymer strands or oligomer strands. The crosslinkage, by means of chemical bonds, can be provided by means of ionic or covaleat bonds. The crosslinking reaction may be any suitable chemical reaction, for example, a salt formation reaction, a condensation reaction, an addition reaction, a substitution reaction or a reaction initiated photochemically or by means of a radical. The crosslinking reaction can occur using suitable catalysts or initiators or the crosslinking reaction can occur without the use of a catalyst. The crosslinking reaction can be initiated by means of a suitable energy source, for example, electromagnetic radiation, ultrasound, heat or mechanical energy. A combination of two or more methods for initiation can be employed in order to increase the efficiency or the velocity of the crosslinking reaction. The crosslinking reaction can, for example, be initiated by means of light-sensitive or temperature-sensitive initiators, by means of red-ox systems or combinations thereof, or the reaction can be initiated without the use of initiators, e.g., using UV light, heat or mechanical energy.

Shape-memory polymers which can be used in accordance with the present invention possess at feast one transition temperature ($T_{trans}$). This transition temperature may be a melting temperature Tm or a glass transition temperature Tg, Above $T_{trans}$, the polymer has a lower modulus of elasticity than below $T_{trans}$. The ratio of the modulus of elasticity below $T_{trans}$ to above $T_{trans}$ is preferably at least 1.1. The transition temperature $T_{trans}$ is the temperature above which the spontaneous recovery of the permanent shape, starting from the deformed shape or the temporary shape, occurs. The transition temperature of the SMP is in the range of about 10° C. to about 80° C., about 15° C. to about 75° C., about 20° C. to about 70° C., about 20° C. to about 60° C., about 20° C. to about 50° C., about 20° C. to about 45° C., about 20° C. to about 40° C., about 20° C. to about 25° C, about 22° C. to about 35° C., about 30° C. to about 40° C., or about 40° C. to about 65° C. The transition temperature $T_{trans}$ is preferably above room temperature (20°C.), preferably tins transition temperature is at least 30° C., in particular preferred 40° C.

The mascara composition containing SMP is applied to eyelashes, followed by heated mascara coder application. The SMP will change shape from straight to curl very quickly. Moreover, tire curling effect will remain permanent. The mascara adheres well to the eyelashes during and after application and provides the eyelashes with good instantaneous loading.

The shape-memory fiber can create long-lasting branched effect for mascara products. The temperature change induced by heated mascara curler can stimulate shape memory fiber to change shape from straight to curl and V-shaped. It can also change from a single fiber to split fiber. The shape change provides branching effect, which has a multitude of benefits to consumers, such as fuller eyelashes. The shape-memory fibers are designed to take advantage of the cross-sectional shapes of fibers.

The shape-memory gels also provide a skin-lifting effect to a skin mask or lotion. This type of hydrogel has considerable shrinkage property upon temperature change. Examples of shape-memory gels are co-polymerized acrylic acid and stearyl acrylate cross-linked with methylenebisacrylamide (NIPA) and sodium acrylate. The gel is swollen below the lower critical solution temperature (LCST) of 37° C. Exceeding this temperature causes shrinkage of the gel, resulting in a skin-lifting effect.

In accordance with the present invention, the skin-lifting mask or lotion composition comprises: 1) an SMP, 2) an oil phase and 3) a water phase.

The SMP may be any SMP as defined herein. The form of the SMP for the skin-lilting composition is preferably a gel. The SMP concentration is between about 1% to about 60%, preferably between about 5% to about 20%.

The water phase of the skin-lifting composition is between about 10% to about 99%, preferably about 30% to about 70%. In addition to water, the water phase may contain additional ingredients such as alkalinzing agents, emulsifying agents, emollients, plasticizers, preservatives, humectants, solvents, and tonicity agents. Examples of preferred additional ingredients include triethanolamine and glycerin.

The oil phase of the skin-lifting composition is between about 1% to about 50%, preferably about 10% to about 25%. The oil phase may consist of emulsifying agents, sohibiiizing agents, lubricants, emollients, viscosity-increasing agents, detergents, surfactants, cleansing agents, thickening agents, anti-oxidants and preservatives.

Methods of Use

One embodiment of the invention is a process for curling the eyelashes, comprising applying a composition, as defined above to the eyelashes with heat, The mascara composition, is so designed to provide suitable physiochemical properties for the usage when heated to a predetermined temperature. Preferably, the temperature change can be introduced by a heated mascara curler, which can raise the temperature of the eyelashes to 40-65° C. However, nothing herein is meant to limit how the SMPs are heated. The SMP composition may be heated by any means such as, but not limited to, light activation, irradiation, magnetic fields, ultrasonic means, electric means, use of photo-sensitive functional groups, pH changes, warm air as in a hair dryer, heated cloth or pad, chemical means or any means which may produce heat. Such chemical means may include a chemical reaction resulting in heat generation. Alternatively, the container holding the composition or accompanying the composition may be heated.

Additionally, the compositions of the invention may be used together with other devices or compositions for curling or branching eyelashes.

Another embodiment is the use of the composition as defined above to curl the eyelashes. The compositions and the process according to the invention are suitable for eyelashes, including false eyelashes.

In one embodiment, the composition of the present invention is a spreadable, flowable and greaseless cosmetic composition useful for, but not limited to, mascara. The composition according to the invention may apply easily and may attach well to eyelashes.

A person skilled in the art can select the appropriate presentation form, and also the method of preparing it, on the basis of general knowledge, taking into account tire nature of the constituents used and the intended use of the composition.

The composition useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

In another embodiment the resulting composition can be employed as it is and can itself constitute a skin care or make-up composition for a face-lifting skin mask or lotion, a make-up base, a top-coat and other cosmetic products. The formulations may be anti-aging, restructuring, stimulating, free-radical scavenger, antioxidant, anti-acne, calming, anti-neuromediator, anti-Substance P, anti-allergic, pain relief, anti-stress, anti-wrinkle, pro-firmness, pro-elasticity, cicatrizing, toning, tensioning, slimming, veinotonic, draining, anti-redness, immunomodulatory, lightening or revitalizing formula, or else formula intended to improve the complexion of the skin, to stimulate the cells or to promote the synthesis of the proteins of the skin, such as collagen or keratin.

The formulations having moisturizing and/or restructuring activity on the epidermis which incorporate a SMP according to the invention may be prepared by the methods conventionally used by those skilled in the art in the cosmetology field or in the dermopharmacy field.

The composition may take the form of a lotion, foam, heated foam, solution, cream, ointment, paste, mask, spray, microbeads, emulsion, aerosol, rigid or soft gel. The composition of the invention may be in the form of a paste, a solid or a more or less viscous cream. Further, the inventive composition may be a single emulsion (such as an oil-in-water or water-in-oil emulsion), a multiple emulsion (such as an oil-in-water-in-oil emulsion or a water-in-oil-in-water emulsion), or a rigid or soft gel comprising an oily continuous phase. For example, in one embodiment, the composition may comprise a liquid fatty phase. In a further embodiment, the liquid fatty phase may be the continuous phase of the composition. In one embodiment, the composition is in the form of a single emulsion. In a further embodiment, the composition is in the form of an oil-in-water emulsion.

Further, according to the present invention, the inventive compositions may be washable compositions, i.e., those that may be removed with wafer and/or soap (e.g., emulsions) or waterproof compositions (e.g., solvent-based compositions), depending on the additional compounds and the desired product. In fact, the inclusion of the at least one film-forming component of the present invention may impart water resistance to an otherwise washable composition and may impart increased water resistance to an otherwise water resistant composition. Thus, in one aspect, the present invention provides a method for making a water resistant composition comprising including in a cosmetic composition at least one film-forming component as defined herein.

The compositions herein can be used by topically applying to the areas of the skin an effective amount of the compositions. The effective amount can easily be determined by each user.

In one embodiment, the skin-lifting composition is applied to skin in need thereof or sagging, loose or thin skin. In a particular embodiment, the composition is applied to the skin of the face. In another embodiment, the composition is applied to skin on the arms, legs, or abdomen.

The composition can be applied for several days, weeks, months or years at any intervals. The compositions are generally applied by light massaging the composition onto the skin. However, the method of application may be any method known in the art and is thus not limited to the aforementioned.

In a particular embodiment, the composition is applied once per day or twice per day. In another embodiment, the more than one layer of the composition is applied.

The composition of the present invention may also include other cosmetic ingredients such as, but not limited to, humectants, emollients, moisturizers, anti-wrinkle ingredients, concealers, matte finishing agents, pigments, colorants, proteins, anti-oxidants, bronzers, chelating agents, emulsifiers, ultraviolet (UV) absorbing agents, oil absorbing agents, anti-foam agents, anti-tack agents, thickeners, fragrances, preservatives, anti-microbials, fungistats, neutralizing agents, vitamins, plasticizers, cohesion agents, basifying and acidifying agents, fillers, solvents, and mixtures thereof. It is understood to those skilled in the art that any other cosmetically acceptable ingredient, i.e., those included in the CFTA Cosmetic Ingredient Dictionary, 3rd ed. may be used.

The composition may also contain at least one cosmetic active ingredient and/or at least one dermatological active ingredient, i.e. an agent having a beneficial effect on the skin or eyelashes. The loading of such active ingredient can be achieved in any means known to those skilled in the art. Suitable methods comprise (a) the combined dissolution of active ingredient and SMP material in a solvent and subsequent drying (alternatively it is possible to precipitate using a non-solvent for both compounds), (b) the mixing of active ingredient and a precursor material for the SMP material, followed by crosslinking of the precursor material (optionally the mixing is carried out with the aid of a solvent which will then be removed), or (c) swelling of objects made from SMP materials in a solution of the active ingredient. Further possibilities for introducing the active ingredient into a matrix are melt mixing (using an extruder), the chemical fixation of the active ingredient onto the matrix molecules or other similar procedures.

On the other hand, it is also possible to employ a controlled release type of active ingredient delivery system. In this respect it also can be achieved that the active ingredient is released over a short period of time, which is desired in some fields of application. In this respect, the matrix material of the active ingredient release system in accordance with the present invention may have the function of a membrane, which, after initiating the shape memory effect, is completely permeable with respect to the enclosed active ingredient, so mat an immediate release becomes possible. Such active ingredient release systems may either be prepared completely of an SMP material, for example in the form of a hollow body which encloses a depot of the active ingredient, or the system consists of a depot system for the active ingredient having an opening, which is closed with the SMP material.

The first alternative is in particular suitable for encapsulating systems, for example, for active ingredients which are to be employed topically. In the field of cosmetic preparations, active agents, such as vitamins, skin care agents or other agents, which are for example susceptible to oxidation, are encapsulated, so that after the application onto the skin, due to the influence of the body temperature, a shape memory effect is initiated liberating the enclosed active ingredient. Other possible fields of application are reservoirs for artificial tears or medicaments for topical application which are encapsulated.

The composition of the invention may also be in the form of a colored make-up product for the skin, such as a foundation, optionally having care or treating properties, a mask, a face powder, a serum, a concealer product, a top or bottom make-up coat, a make-up product for the body; a make-up product for the lips such as a lipstick, optionally having care or treating properties; a make-up product for the eyelashes, for example, in the form of a mascara cake, wand, or pencil.

Needless to say, the composition of the invention should be cosmetically or dermatologically acceptable, i.e., it should contain a non-toxic physiologically acceptable medium and should be able to be applied to the skin, superficial body growths or the lips of human beings. For the purposes of the invention, the expression "cosmetically acceptable" means a composition of pleasant appearance, odor, feel and taste.

A person skilled in the art will take care to select the optional additives and/or the amount thereof such that the advantageous properties of the composition according to the invention are not, or are not substantially, adversely affected by the envisaged addition. It is further understood that the other cosmetic ingredients and adjuvants introduced into the composition must be of a kind and quantity that are not detrimental to the advantageous effect which is sought herein according to the invention.

The following examples describe specific aspects of the invention to illustrate the invention and provide a description of the present methods for those skilled in the art. The Examples should not be construed as limiting the invention as the examples merely provide specific methodology useful in the understanding and practice of the invention and its various aspects.

The following contemplated examples are offered solely for the purpose of illustrating the invention and are not indicated to limit the scope of the invention in any respect.

EXAMPLES

It is to be understood by those skilled in the art that while certain preferred and alternative embodiments of the invention have been set forth for purposes of disclosing the invention, modification to the disclosed embodiments can occur.

Example 1

Mascara Composition with Shape Memory Polymer (SMP) Fiber

A mascara composition containing SMP for application to the eyelashes or hair was prepared with the following formulation and procedure:

|  | Ingredient | Amount (%) |
| --- | --- | --- |
| Water Phase | Deionized Water | 57.23 |
|  | Methylparaben | 0.2 |
|  | Polyvinylpyrrolidone | 15 |
|  | Magnesium Silicate | 075 |
|  | Triethanolamine 99 | 0.4 |
|  | Iron Oxide(Black) Silica/BHT | 9 |

-continued

|  | Ingredient | Amount (%) |
| --- | --- | --- |
| Oil Phase | Propylparaben | 412 |
|  | Cetyl Alcohol | 0.3 |
|  | Glyceryl Monostearate | 3.2 |
|  | Paraffin Wax 165 | 1.5 |
|  | Carnauba Wax | 1.5 |
|  | Cetearyl Alc./Ceteth-20 PH | 1.8 |
|  | Beewax | 6.5 |
|  | Phenoxyethanol-98% MIN | 0.5 |
| SMP Phase | Shape-Memory Fiber | 2 |
|  | Total | 100 |

1. The ingredients of the oil phase are heated to 80-85° C. while mixing until uniformly mixed.

2. The ingredients of the water phase are heated to 80-85° C. while mixing until uniformly mixed.

3. The water phase is added to the oil phase with high-speed homogenization mixing for 15 minutes.

4. The mixture is then allowed to cool down to room temperature, and the SMP phase is added while mixing.

Example 2

Skin Lift Lotion Composition with Shape Memory Polymer (SMP) Gel

A composition containing SMP for application to skin was prepared with the following formulation and procedure:

|  | Ingredients | Amount (%) |
| --- | --- | --- |
| Oil Phase | Stearic Acid | 0.6 |
|  | Cetearyl Glucoside & Cetearyl alcohol | 2.5 |
|  | Glyceryl Stearate | 2 |
|  | Isohexadecane | 4.5 |
|  | Caprylic/Capric Triglyceride | 3 |
|  | Petrolatum | 4 |
|  | Shea Butter | 0.5 |
|  | Tocopherol Acetate | 0.5 |
|  | Sodium Polyacrylate | 0.3 |
| Water Phase | Glycerine | 5 |
|  | Triethanolamine | 0.3 |
|  | Water | 61.8 |
| SMP Phase | Shape-Memory Polymer Gel | 15 |
|  | Total | 100 |

1. The ingredients of the oil phase are heated to 80-85° C. while mixing until uniformly mixed.

2. The ingredients of the water phase are heated to 80-85° C. while mixing until uniformly mixed.

3. The water phase is added to the oil phase with high-speed homogenization mixing for 15 minutes.

4. The mixture is then allowed to cool down to room temperature, and the SMP phase is added while mixing.

Example 3

Comparison of Thermal Effects of a Convention Mascara Composition and a SMP-Containing Mascara Composition A conventional mascara composition and a shape memory polymer (SMP) containing mascara composition were prepared with following formulations:

| Ingredient | Conventional Mascara | Mascara with SMP |
|---|---|---|
| Deionized Water | 33.42 | 34.5 |
| Disodium EDTA | 0.1 | |
| Sodium CMC | 1 | |
| Polyvinyl Alcohol | 10 | |
| Propylparaben | 0.2 | |
| Methylparaben | 0.38 | 0.5 |
| Triethanolamine | 1.5 | |
| Iron Oxides-Black Disp. in Acrylates Cop/AMP/Pres. | 45 | 45 |
| Isoceteth-20 | 0.5 | |
| Oleth-3 Phosphate | 0.5 | |
| Palmitic Acid | 4 | |
| Stearic Acid | 2 | |
| Phenoxyethanol-98% Min | 0.4 | |
| Triisostreayl Trinoleate | 0.5 | |
| SMP Polymer | 0 | 20 |

The shape memory polymer used in the composition of Example 3 is block copolymer of polyethyleneoxide-polypropyleneneoxide-polyethyleneoxide (PEO-PPO-PEO) with urethane/urea units.

Rheology profiles of mascara with and without SMP polymer, as well as SMP solution in water, are shown in FIG. 1. Most conventional mascara compositions have a rheology profile of decreased viscosity with increased temperature, i.e., a thermal thinning effect. By incorporating SMP into a mascara composition, the rheology profile changes to increased viscosity with increased temperature from 25° C. to 55° C., i.e., a thermal thickening effect. The transition temperature ($T_{trans}$) of 7% shape memory polymer (SMP) in water solution was observed to be 25° C.

Figure 2:
FIG. 2 shows photographs of eyelash curling effect before (left photograph) and after treatment with a SMP-containing mascara composition (center photograph), as well as the curling effect of SMP-containing mascara heated by applicator (right photograph).

Photographs of eyelash curling effect before (left photograph) and after treatment with SMP-containing mascara composition (center photograph), as well as mascara heated by applicator (right photograph), are shown in FIG. 2. From left to right, the first two photographs of FIG. 2 show eyelashes before (left) and after treatment with SMP-containing mascara composition (middle) at ambient temperature. Similar to conventional mascara compositions, there is no significant curling effect. In the last photograph (right), the treated eyelashes show significant curling effect after heating with a mascara applicator at 50° C. The thermal thickening effect enhances the curling effect of the mascara composition.

The invention claimed is:

1. A composition for providing a skin-lifting effect to the skin of the face comprising a hydrogel comprising:
   (i) about 1% to about 60% by weight of a shape memory polymer (SMP), wherein said SMP is a co-polymerized acrylic acid and stearyl acrylate polymer cross-linked with methylenebisacrylamide and sodium acrylate;
   (ii) about 1% to about 50% by weight of an oil phase; and
   (iii) about 10% to about 99% by weight of a water phase.

2. A method for lifting the skin of the face comprising:
   (i) applying to the skin of the face of an individual in need thereof, a composition comprising a hydrogel according to claim 1.

* * * * *